US012352939B2

(12) United States Patent
Heidemann

(10) Patent No.: US 12,352,939 B2
(45) Date of Patent: Jul. 8, 2025

(54) OPTICAL SYSTEM, OPTICAL DELAY LINE AND OCT APPARATUS

(71) Applicant: OPTOS PLC, Dunfermline (GB)

(72) Inventor: Rainer Heidemann, Dunfermline (GB)

(73) Assignee: OPTOS PLC, Dunfermline (GB)

(*) Notice: Subject to any disclaimer, the term of this patent is extended or adjusted under 35 U.S.C. 154(b) by 1139 days.

(21) Appl. No.: 16/837,343

(22) Filed: Apr. 1, 2020

(65) Prior Publication Data
US 2020/0319440 A1 Oct. 8, 2020

(30) Foreign Application Priority Data
Apr. 5, 2019 (EP) .................................... 19167533

(51) Int. Cl.
*G02B 17/02* (2006.01)
*A61B 3/10* (2006.01)
(Continued)

(52) U.S. Cl.
CPC ............ *G02B 17/023* (2013.01); *A61B 3/102* (2013.01); *G02B 17/04* (2013.01); *G02B 17/06* (2013.01);
(Continued)

(58) Field of Classification Search
CPC .... G02B 17/004; G02B 17/023; G02B 17/04; G02B 17/08; G02B 17/0856; G02B 5/122; G02B 5/12–136; G02B 2207/117
See application file for complete search history.

(56) References Cited

U.S. PATENT DOCUMENTS 3,775,012 A * 11/1973 Ling .................. G01B 11/0691
356/152.3
4,266,847 A * 5/1981 Menke ..................... H04N 3/09
348/E3.01
(Continued)

FOREIGN PATENT DOCUMENTS

CH 108 415 154 A 8/2018
CH 108 563 006 A 9/2018
(Continued)

OTHER PUBLICATIONS

Japanese Notice of Reasons for Refusal issued May 28, 2021 in Japanese Patent Application No. 2020-068566 (Machine English language translation attached).
(Continued)

*Primary Examiner* — Nicholas R. Pasko
(74) *Attorney, Agent, or Firm* — FAEGRE DRINKER BIDDLE & REATH

(57) ABSTRACT

An optical system, capable to admit a light beam, the optical system comprising: a plurality of reflectors configured to reflect the light beam, wherein each of the reflectors is configured to reflect an incident light beam such that the path of the incident light beam and the path of the reflected light beam are parallel to each other. Each of the reflectors has a reflection center axis positioned centrally between the path of the incident light beam and the path of the reflected light beam. At least two of the reflectors are arranged relative to each other such that their respective reflection center axes do not overlap, thereby enabling the path of the light beam to pass at least one of the at least two of the reflectors multiple times.

20 Claims, 7 Drawing Sheets

(51) Int. Cl.
    *G02B 17/04*      (2006.01)
    *G02B 17/06*      (2006.01)
    *G02B 17/08*      (2006.01)
(52) U.S. Cl.
    CPC .... *G02B 17/0856* (2013.01); *G02B 2207/117* (2013.01)

(56) References Cited

U.S. PATENT DOCUMENTS

| | | | | |
|---|---|---|---|---|
| 5,220,463 | A * | 6/1993 | Edelstein | G02B 5/12 359/857 |
| 6,003,997 | A * | 12/1999 | Downes, Jr. | G02B 6/2861 359/857 |
| 6,147,799 | A * | 11/2000 | MacDonald | G02B 26/06 359/857 |
| 8,736,843 | B2 | 5/2014 | Medhat et al. | |
| 11,353,660 | B2 * | 6/2022 | Boutin | G02B 6/4292 |
| 2006/0146334 | A1 | 7/2006 | Cluff et al. | |
| 2009/0279171 | A1 | 11/2009 | Stenton | |
| 2010/0265512 | A1 | 10/2010 | Medhat et al. | |
| 2016/0003606 | A1 | 1/2016 | Okano et al. | |
| 2016/0059347 | A1 * | 3/2016 | Kogel-Hollacher | B23K 26/082 219/121.73 |
| 2020/0388979 | A1 * | 12/2020 | Zajdman | G02B 17/004 |

FOREIGN PATENT DOCUMENTS

| | | |
|---|---|---|
| CN | 2682437 Y | 3/2005 |
| CN | 105891958 A | 8/2016 |
| DE | 40 06 407 A1 | 9/1991 |
| GB | 0858171 A | 1/1961 |
| JP | 53-42878 A | 4/1978 |
| JP | H02-067935 A | 3/1990 |
| JP | 02-249955 A | 10/1990 |
| JP | H05-173075 A | 7/1993 |
| JP | H09-159919 A | 6/1997 |
| JP | 2016-017762 A | 2/2016 |
| JP | 2016-206529 A | 12/2016 |
| WO | WO-2011016613 A1 * | 2/2011 .......... G02B 17/023 |

OTHER PUBLICATIONS

"First Office Action", which is an English translation of Office Action issued Jan. 29, 2022 in Chinese No. 202010264282.1 (7 sheets).

Communication and European Search Report issued Oct. 11, 2019 in application No. EP 19 167 533.9.

Decision to Grant a Patent dated Aug. 29, 2022, issued in Japanese Application No. 2020-068566 (1 sheet) (English translation attached—2 sheets).

Notice of Reasons for Rejection issued Jan. 25, 2022 in Japanese Patent Application No. 2020-068566 (3 sheets) (English Machine Translation attached; 3 sheets).

Office Action issued Jan. 29, 2022 in Chinese No. 202010264282.1 (8 sheets).

Communication pursuance to Article 94(3) EPC issued on Jan. 23, 2024.

* cited by examiner

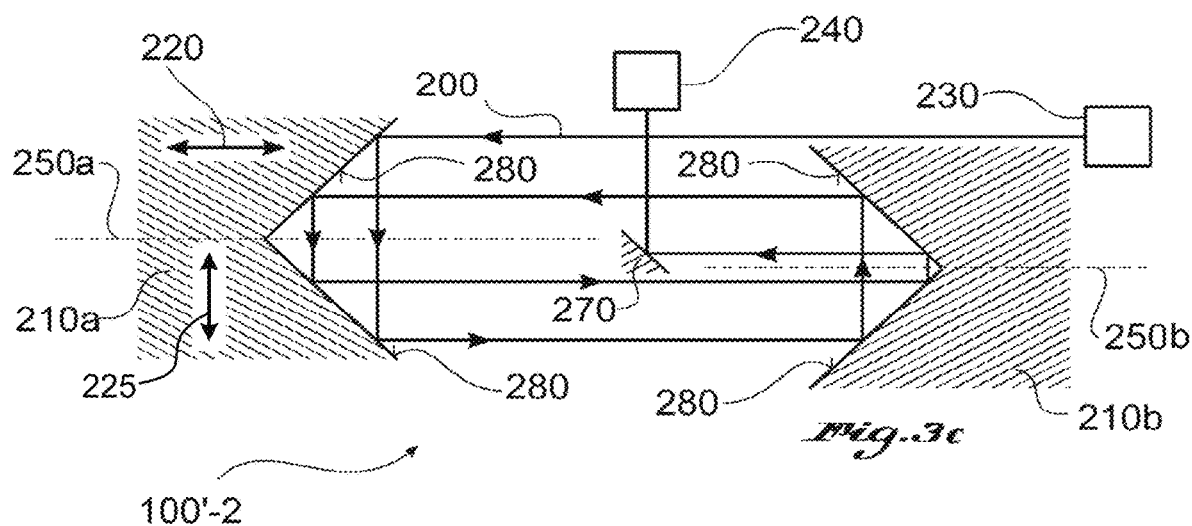
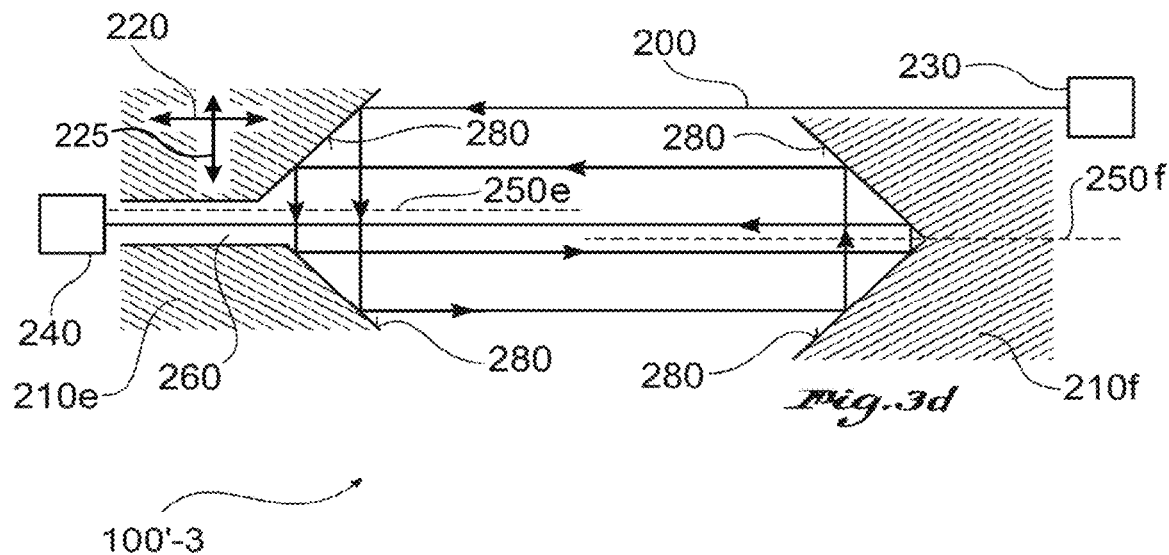

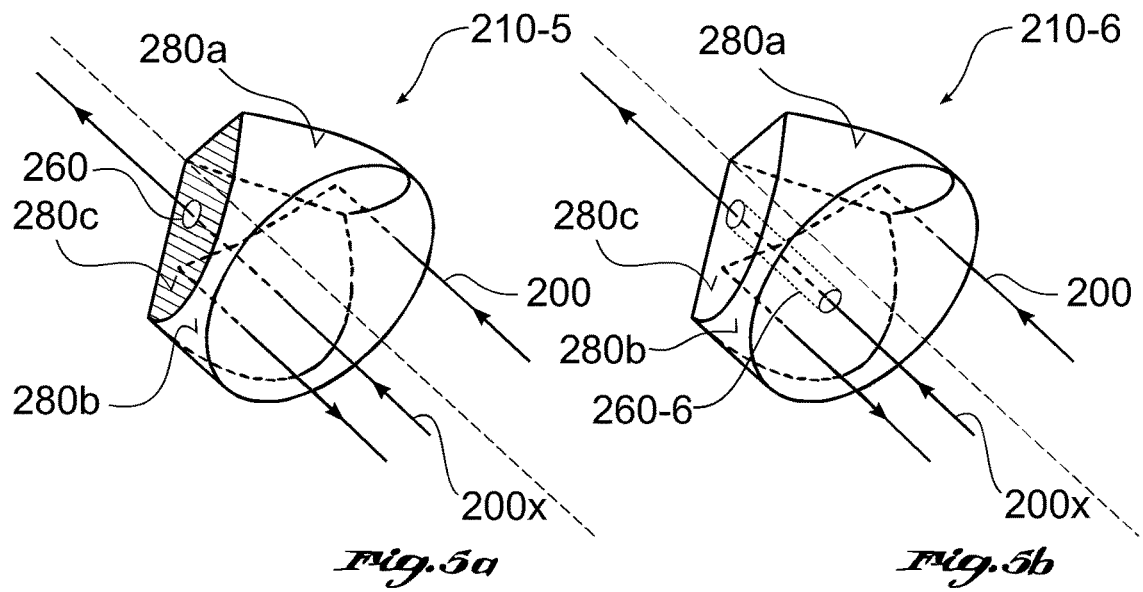
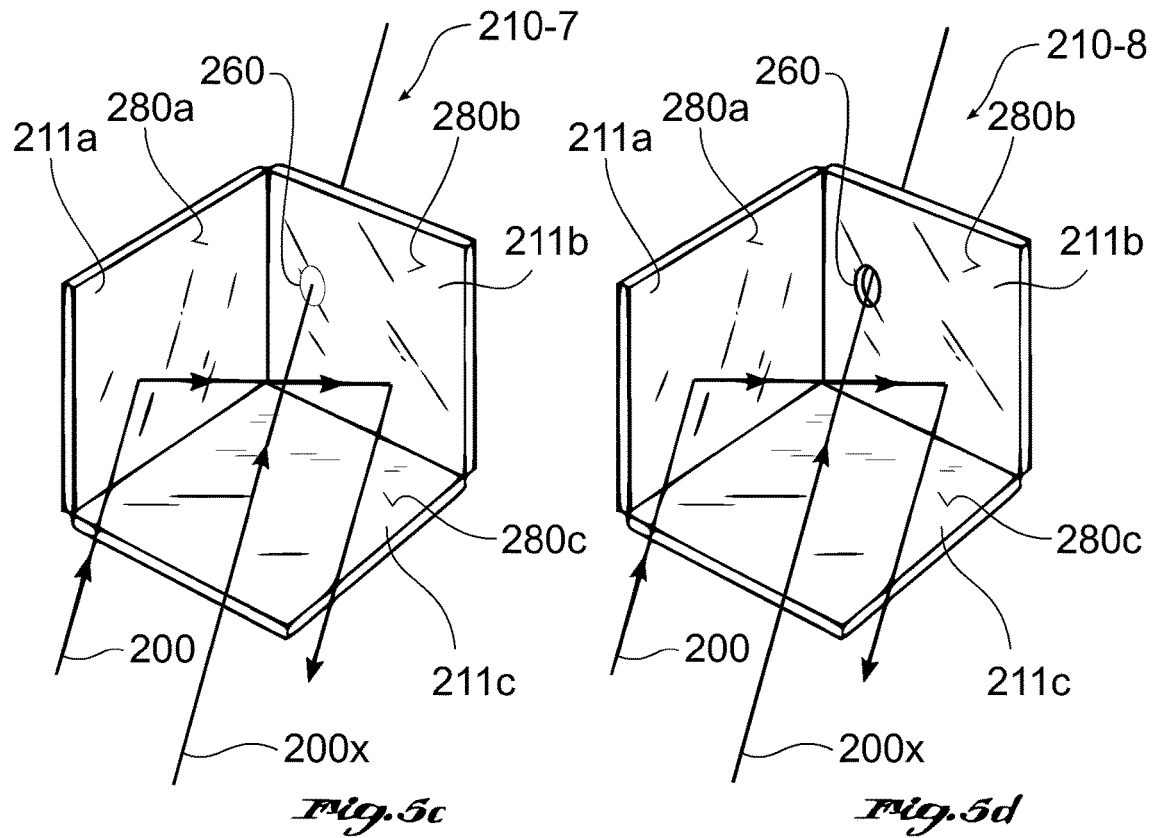

OPTICAL SYSTEM, OPTICAL DELAY LINE AND OCT APPARATUS

This application claims the benefit of priority of European Patent Application No. 19 167 533.9, filed Apr. 5, 2019, the entire contents of which are incorporated by reference as if set forth fully herein.

FIELD

Example aspects herein generally relate to an optical system, an optical delay line having the optical system and an optical coherence tomography (OCT) apparatus having the optical system or the optical delay line.

BACKGROUND

When optical information of a substrate is acquired by means of an OCT apparatus or the like, light of a reference light beam may be desired to travel a relatively long distance in order to provide particular light interference patterns.

A schematic illustration of one example of an OCT apparatus is depicted in FIG. 1. Such an OCT apparatus 10 may comprise a light source 20 configured to provide a light beam 200, a first collimator device 30 configured to collimate the light beam 200 provided by the light source 20 and at least one beam splitter 40 configured such that the light beam 200 incident on the beam splitter 40 is partially reflected by, and partially transmitted through, the beam splitter 40.

One of the reflected and transmitted light beams may be incident on and reflected by a substrate 70. The other one of the reflected and the transmitted light beams may be incident on and reflected by a reflector 80.

Before being incident on and reflected by the substrate 70, the light beam 200 may be reflected by a scanning mirror 50 configured to be movable in one or more directions. Also, a second collimator device 60 may be provided, which is configured to collimate the light beam that is incident on and reflected by the substrate 70.

The OCT apparatus may further comprise a detector unit 90 configured to detect light of the light beam that has been reflected by the substrate 70 and light of the light beam reflected by the reflector 80.

The detector unit 90 may be configured to detect interference patterns between the light reflected by the substrate 70 and the light reflected by the reflector 80. The detector unit 90 may be configured to obtain depth information of the substrate 70 based on the interference patterns.

In such an apparatus, interference patterns that allow obtaining depth information of the substrate 70 arise if the light reflected by the reflector 80 has exceeded its coherence length, which is the length required to match a sample arm of the apparatus. Hence, an optical system 100 may be include in the OCT apparatus 10, which provides a relatively long travel distance for the light beam propagating through it. Such an optical system 100 may be referred to as reference arm or optical delay line.

Because an optical delay line providing relatively long distances may be included in respective apparatuses, each apparatus including such an optical delay line tends to be large.

In order to reduce the size of an optical apparatus having an optical delay line, mirror arrangements reflecting a light beam may be provided. Such mirror arrangements may utilize reflectors having retroreflective properties. That is, the light beam incident on a reflector having retroreflective properties and the light beam reflected from the reflector are in parallel. The term "parallel" herein is not necessarily used in a narrow sense to mean that the light beams (or other entities) being referred to are perfectly parallel but encompasses example embodiments in which these are substantially parallel, the degree of parallelism being sufficient to achieve at least some of the related advantages described herein.

FIG. 2a illustrates an example arrangement of the conventional optical system 100. In the optical arrangement 100, the length of the travelling path of the light beam 200 may be defined, e.g. by the distance between a light input device 230 and a light output device 240. Hence, if a relatively long travelling path of the light beam 200 is to be achieved, a relatively long distance between the light input device 230 and the light output device 240 has to be provided. However, as depicted in the second comparative example of FIG. 2b, the travelling path of the light beam 200 may be extended, without significantly increasing the size of the optical system, by using a reflector 210 having retroreflective properties. As depicted in FIG. 2b, the reflector 210 in this first variant, 100-1, of the conventional optical system may be configured to be movable in an adjustment direction 220. Furthermore, utilizing multiple reflectors 210 having retroreflective properties allows for providing an even longer light beam path, without significantly increasing the size of the optical arrangement, as illustrated in the second comparative example of FIG. 2c, which illustrates a second variant, 100-2, of the conventional optical system.

However, reflectors having retroreflective properties are typically heavy. Hence, decreasing the size of an optical delay line by providing multiple reflectors having retroreflective properties may increase the weight of the apparatus, making it less easily portable.

SUMMARY

The present inventors have devised, in accordance with a first example aspect herein, an optical system, capable to admit a light beam. The optical system comprises a plurality of reflectors configured to reflect the light beam, wherein each of the reflectors is configured to reflect an incident light beam such that the path of the incident light beam and the path of the reflected light beam are parallel to each other. Each of the reflectors has a reflection center axis positioned centrally between the path of the incident light beam and the path of the reflected light beam. At least two of the reflectors are arranged relative to each other such that their respective reflection center axes do not overlap, thereby enabling the path of the light beam to pass at least one of the at least two of the reflectors multiple times.

The present inventors have also devised, in accordance with a second example aspect herein, an optical delay line for an optical coherence tomography apparatus, the optical delay line comprising the optical system according to the first example aspect herein.

The present inventors have also devised, in accordance with a second example aspect herein, an optical coherence tomography apparatus comprising at least one of the optical system according to the first example aspect herein, or the optical delay according to the second example aspect herein.

BRIEF DESCRIPTION OF THE DRAWINGS

Embodiments of the invention will now be explained in detail, by way of non-limiting example only, with reference to the accompanying drawings, the contents of which are described below. Like reference numerals appearing in different figures of the figures denote identical, corresponding or functionally similar elements, unless indicated otherwise.

FIG. 3c is a schematic illustration of a second embodiment of an optical system according to the first example aspect herein.

FIG. 3d is a schematic illustration of a third embodiment of an optical system according to the first example aspect herein.

FIG. 5a illustrates an example of a first variant of the second type of reflector utilizable in some embodiments of the optical system according to the first example aspect herein.

FIG. 5b illustrates an example of a second variant of the second type of reflector utilizable in some embodiments of the optical system according to the first example aspect herein.

FIG. 5c illustrates an example of a third variant of the second type of reflector utilizable in some embodiments of the optical system according to the first example aspect herein.

FIG. 5d illustrates an example of a fourth variant of the second type of reflector utilizable in some embodiments of the optical system according to the first example aspect herein.

DETAILED DESCRIPTION OF EMBODIMENTS

Exemplary embodiments herein will now be described in detail with reference to the accompanying drawings.

Embodiment 1

Figure 1:
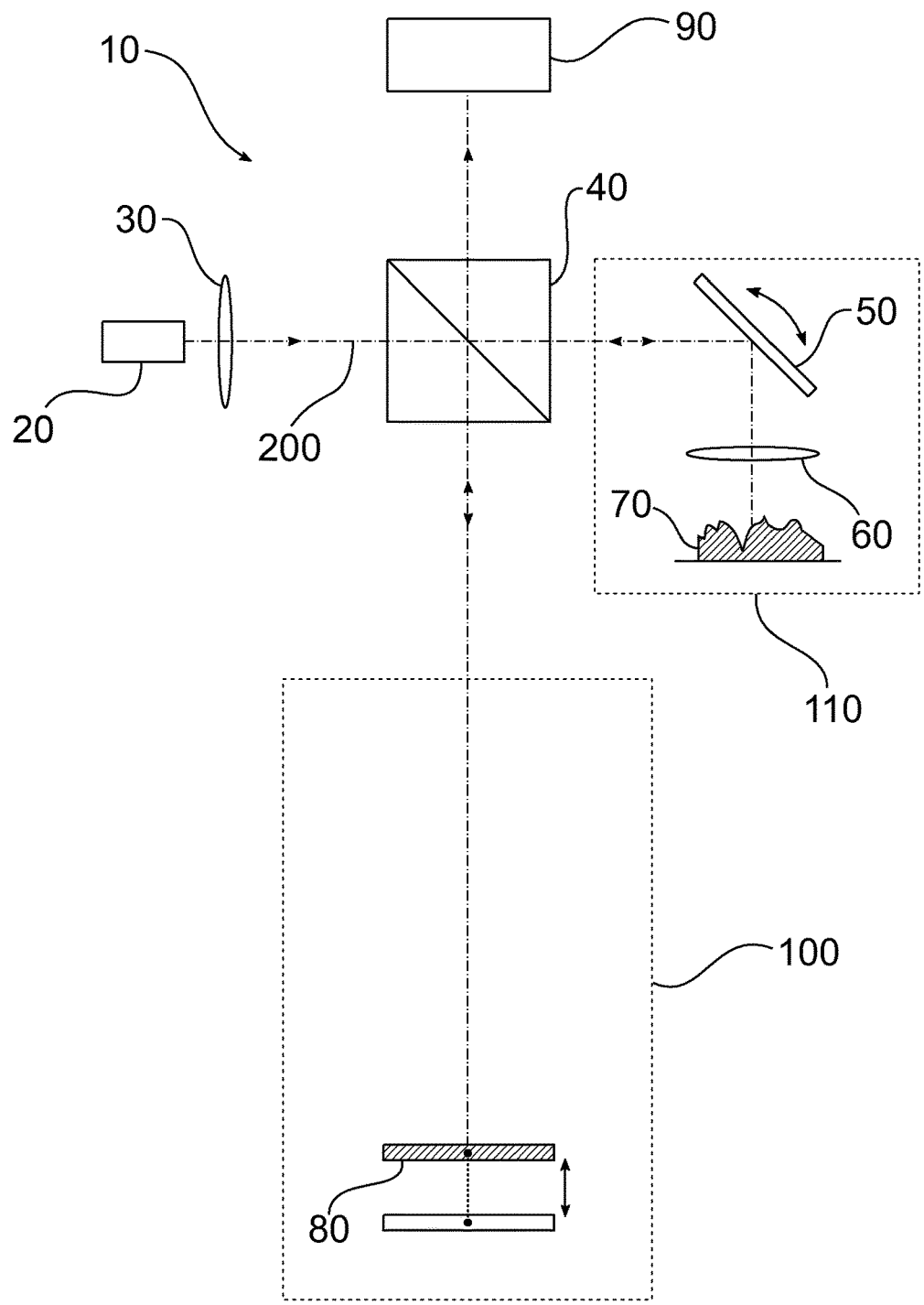
FIG. 1 is a schematic illustration of an example of an optical coherence tomography apparatus.
Figure 2A:
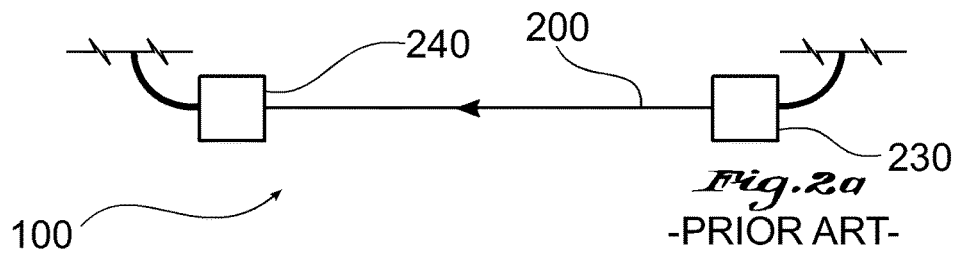
FIG. 2a is a schematic illustration of a first comparative example of an optical delay line suitable for use in an optical coherence tomography apparatus.
Figure 2B:
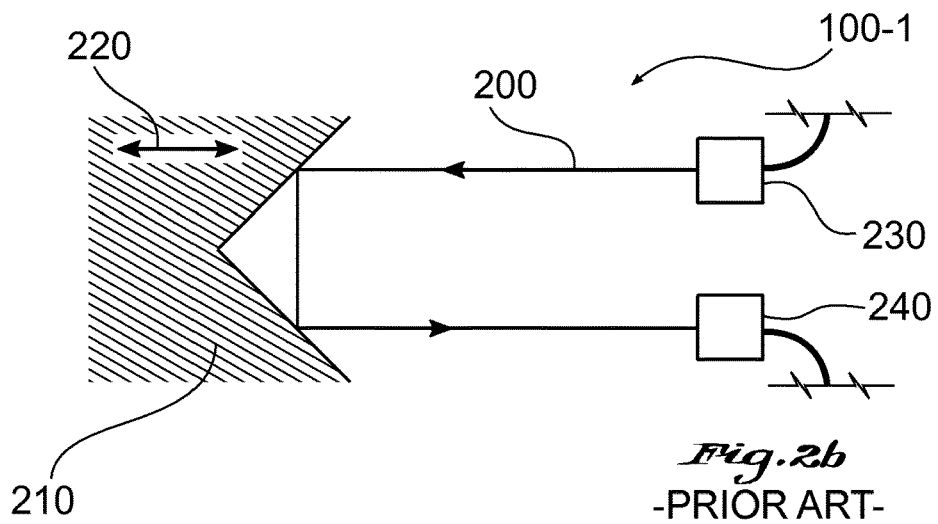
FIG. 2b is a schematic illustration of a second comparative example of an optical delay line suitable for use in an optical coherence tomography apparatus.
Figure 2C:
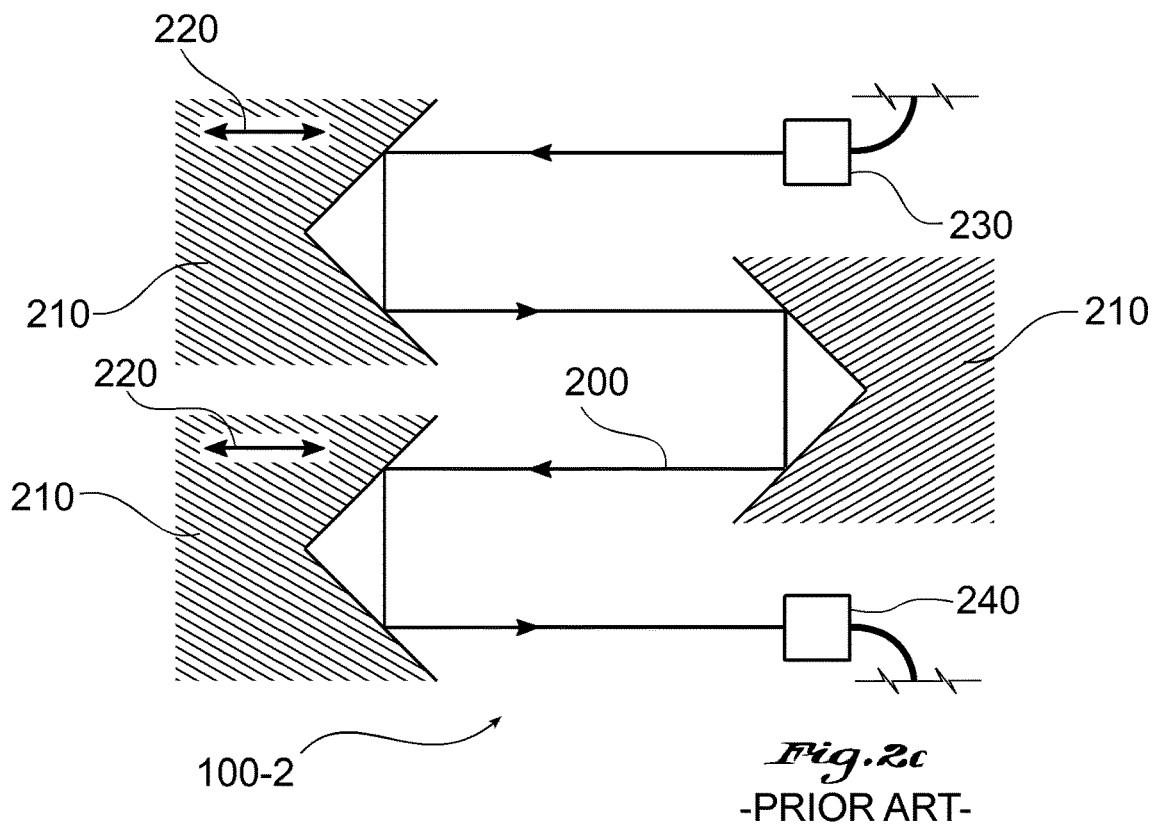
FIG. 2c is a schematic illustration of a third comparative example of an optical delay line suitable for use in an optical coherence tomography apparatus.
Figure 3A:
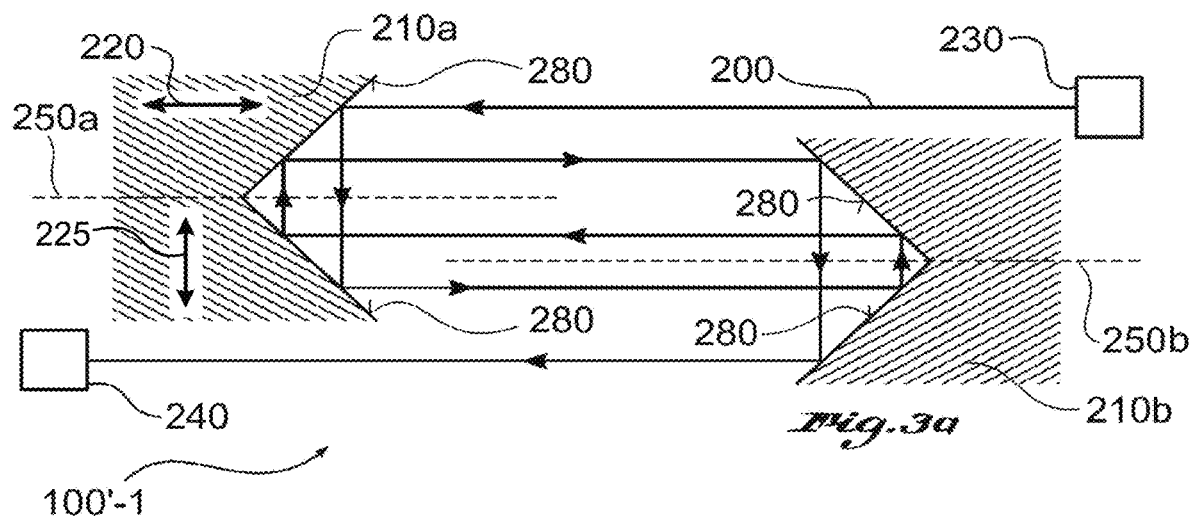
FIG. 3a is a schematic illustration of a first embodiment of an optical system according to a first example aspect herein.

FIG. 3a is a schematic illustration of an optical system 100'-1 according to a first example embodiment of the first example aspect herein, which represents an improvement of the conventional optical system 100. The optical system 100'-1 may replace the conventional optical system 100 forming part of a conventional OCT apparatus 10 as illustrated in FIG. 1, resulting in an improved OCT apparatus 10', as described further below with reference to FIG. 6.

In the optical system 100'-1, a light beam 200 provided by a light source (not shown in FIG. 3a) is incident on a reflector 210a having reflective surfaces 280. The reflector 210a is configured to reflect the light beam 200 such that the portion of the light beam 200 incident on the reflector 210a and the portion of the light beam 200 reflected by the reflector 210a are parallel to each other. The optical system 100'-1 further comprises a second reflector 210b, as also illustrated in FIG. 3a.

It is noted that, between the state of being incident on a reflector (210a or 210b) and the state of being reflected from a reflector, one or more additional reflections of the light beam 200 inside or on the reflector may occur. A light beam being incident on a reflector, then optionally being reflected one or more times inside of the reflector, followed by being reflected from the reflector such that the portion of the light beam incident on the reflector and the portion of the light beam reflected from the reflector are parallel to each other may be referred to as a light beam passing one reflector (or a "light beam pass"). Each reflector may be configured such that the optical path of the portion of the light beam 200 that is incident on the reflector and the optical path of the portion of the light beam 200 that is reflected by the reflector have a minimum separation that does not equal zero.

In the first example embodiment depicted in FIG. 3a, the light beam reflected from the reflector 210a is incident on the reflector 210b, which is also configured to reflect an incident light beam 200 such that the incident portion of the light beam 200 and the reflected portion of the light beam 200 are parallel to each other. Hence, after being incident on and reflected by the reflector 210b, the light beam 200 travels back to the reflector 210a. The light beam 200 then, again, passes the reflector 210a such that it travels back to the reflector 210b. However, after again passing the reflector 210b, the light beam 200 travels beyond the reflector 210a, as illustrated in FIG. 3a. In other words, after being reflected from the reflector 210b for the second time, the light beam 200 is not incident on, but travels alongside, the reflector 210a.

In the first example embodiment shown in FIG. 3a, the cumulated number of light beam passes is four. It is noted that the number of passes depicted in FIG. 3a is given by way of example only, and should not be understood as limiting. In the same way, 10, 100, 1000 or any other number of passes may be utilized. If only two reflectors are provided, the number of passes associated with one of the two reflectors, and the number of passes associated with the other of the two reflectors, may be the same or may differ by 1. In the configuration of FIG. 3a, the light beam 200 will make an even number of passes before exiting the optical system 100'-1. In such a configuration, the light beam 200 may exit the optical system 100'-1 in the same direction (forward direction) in which it entered the optical system 100'-1. In other configurations, the light beam may make an odd number of passes before exiting the optical system. In such configurations, the light beam may exit the optical system in a reverse direction to the direction in which it entered the optical system.

In the optical system 100'-1 according to the first example embodiment, the reflector 210a, on which the light beam 200 provided by the light source (not shown in FIG. 3a) is incident first before being incident on the reflectors 210*b*, may be regarded as the first reflector. Further, the reflector 210*b*, from which the light beam 200 is reflected last, such that after reflection from reflector 210*b*, the light beam 200 is not incident on any other reflector, may be regarded as the last reflector. In the configuration of FIG. 3*a*, the first reflector 210*a* and the last reflector 210*b* are different reflectors, but in other configurations, the first reflector and the last reflector may be the same reflector.

Figure 3B:
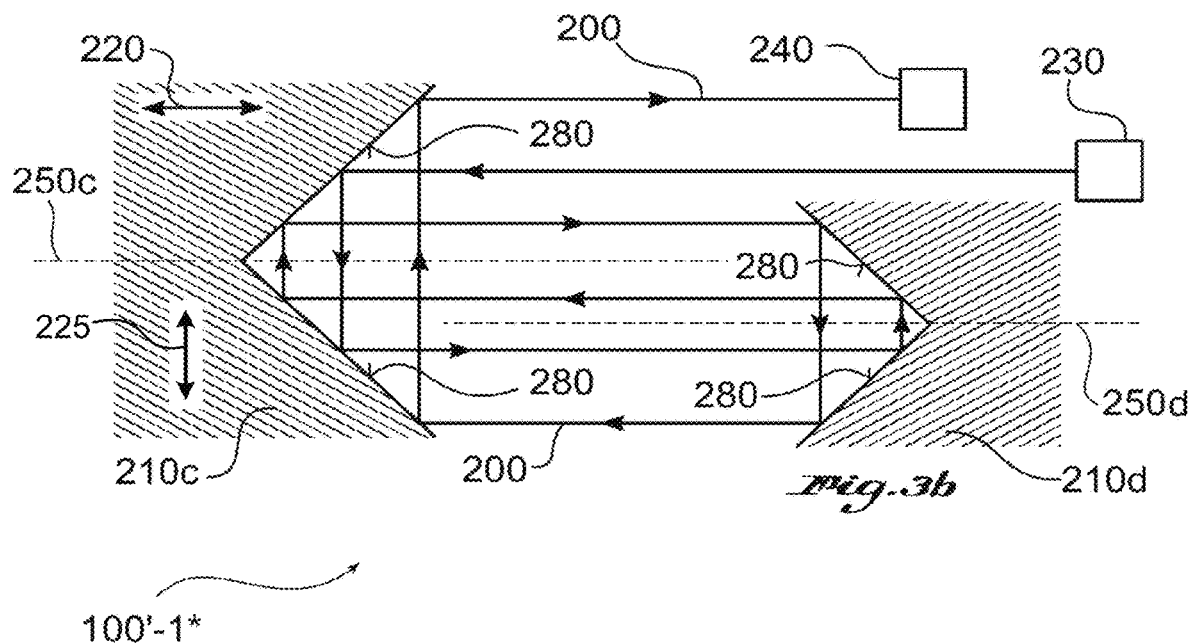
FIG. 3b is a schematic illustration of a variant of the first embodiment of the optical system according to the first example aspect herein.

For example, FIG. 3*b* illustrates an optical system 100'-1* according to a variant of the first example embodiment is illustrated schematically in FIG. 3*b*, in which the reflector 210*c* functions both as the first reflector and the last reflector. That is, the reflector 210*c* is the first reflector to be passed by the light beam 200 and also the last reflector to be passed by the light beam 200.

Optionally, the portion of the light beam 200 first incident on the first reflector, 210*a* or 210*c*, may emerge from a light input device 230, such as an input fibre collimator. Further, optionally, the portion of the light beam 200 last reflected from the last reflector, 210*b* or 210*c*, may be incident on a light output device 240, such as an output fibre collimator.

As depicted in FIG. 3*a* and FIG. 3*b*, each of the reflectors 210*a*, 210*b*, 210*c*, 210*d* (hereafter referred to by the numeral 210, where it is unnecessary to distinguish between them) has a respective center axis, 250*a*, 250*b*, 250*c* and 250*d*, positioned centrally between the incident portion of the light beam 200 and the reflected portion of the light beam 200. The centre axis (hereafter referred to by the numeral 250, where it is unnecessary to distinguish between the centre axes of different reflectors) may be an axis of rotational symmetry of the reflector 210, or may be an axis in a plane of reflection symmetry of the reflector 210, optionally an axis of intersection of planes of reflection symmetry of the reflector 210. The centre axes 250*a* and 250*b* of the two reflectors 210*a* and 210*b*, and the centre axes 250*c* and 250*d* of the two reflectors 210*c* and 210*d*, do not overlap. It is noted that arranging reflectors such that the respective centre axes do not overlap may avoid the light beam 200 being trapped in an infinite loop between the reflectors.

Figure 4A:
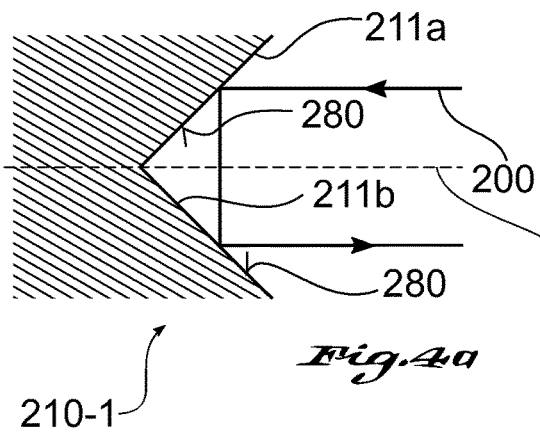
FIG. 4a illustrates an example of a first type of reflector utilizable in an optical system according to an example embodiment herein.
Figure 4B:
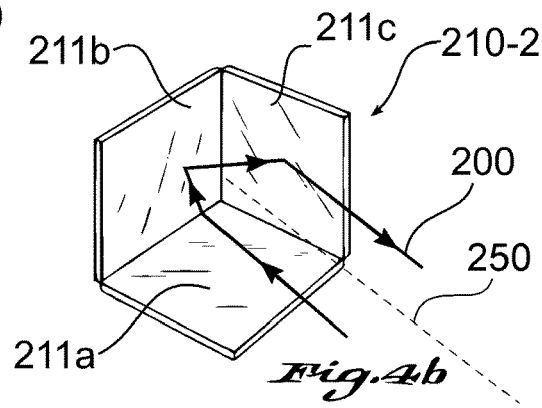
FIG. 4b illustrates an example of a second type of reflector utilizable in an optical system according to an example embodiment herein.
Figure 4C:
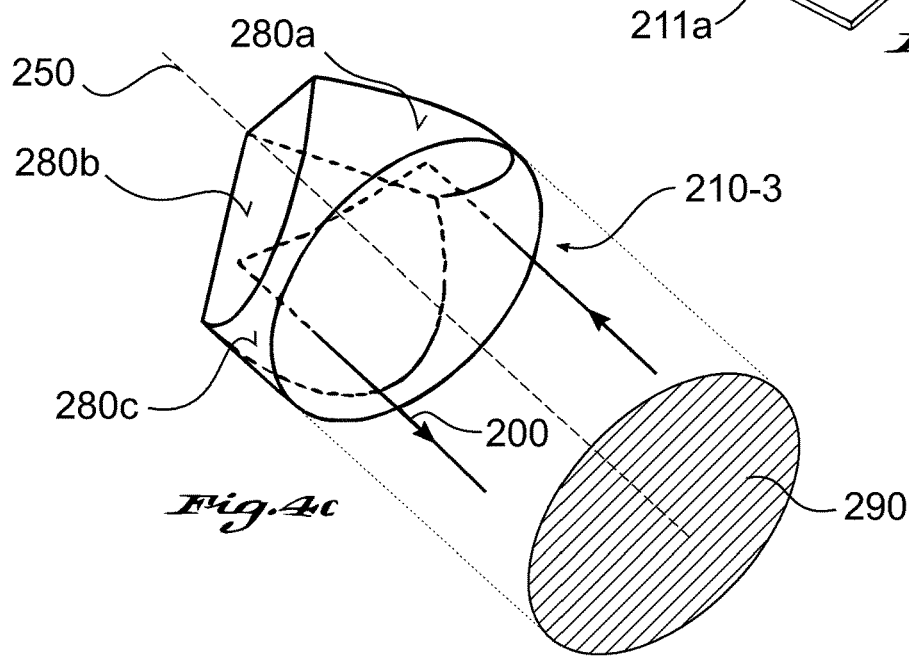
FIG. 4c illustrates an example of a third type of reflector utilizable in the optical system according to the first example aspect herein.
Figure 4D:
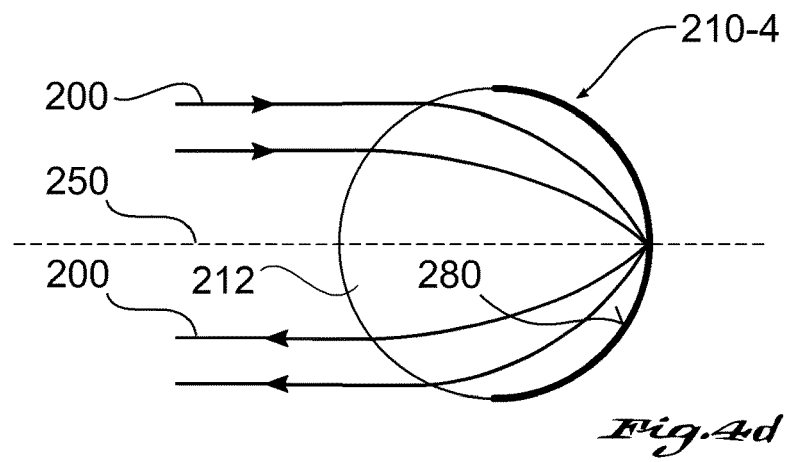
FIG. 4d illustrates an example of a fourth type of reflector utilizable in an optical system according to an example embodiment herein.

In the optical system 100'-4 according to the first embodiment or in the variant thereof, 100'-1*, which is illustrated in FIG. 3*b*, each reflector 210 may be a mirror arrangement 2104 comprising only two mirrors that are orthogonal to each other, for example as shown at 211*a* and 211*b* in FIG. 4*a*. Each reflector 210 may alternatively be a corner cube 210-2 comprising three mirrors, for example as shown at 211*a*, 211*b* and 211*c* in FIG. 4*b*. In such a corner cube 210-2, each of the three mirrors 211*a*, 211*b*, 211*c* is orthogonal to the other two of the three mirrors. As a further alternative, each reflector 210 may take the form of a corner cube prism 210-3, as depicted in FIG. 4*c*. The corner cube prism 210-3 may comprise three reflective surfaces 280*a*, 280*b*, 280*c*, each of which is orthogonal to the other two reflective surfaces. As a yet further alternative, each reflector 210 may take the form of a Luneburg lenses. A Luneburg lens 210-4 may, as depicted in FIG. 4*d*, comprise a spherical body 212 and a reflective surface 280. A Luneburg lens may be regarded as a spherically symmetric gradient-index lens, the refractive index of which decreases radially from the center to the outer surface. Moreover, portions of the surface of a Luneburg lens (e.g. the reflective surface 280 depicted in FIG. 4*d*) may be configured to reflect a light beam 200 incident from the inside of the respective sphere.

Alternatively, or additionally, a retroreflective film may be utilized as reflector 210. A retroreflective film may, for example, comprise multiple miniature-sized Luneburg lenses, corner cubes or corner cube prims. Also, the optical system 100'-1 according to the first embodiment herein, or the optical system 100'4* according to a variant of the first embodiment, may comprise a combination of two or more of the reflector types mentioned above, e.g. Luneburg lenses, corner cube prisms, etc.

Mirror arrangements comprising only two orthogonal mirrors may be advantageous due to their simplicity and associated ease of manufacture. However, to achieve the effect wherein the incident portion of the light beam 200 and the reflected portion of the light beam 200 are parallel, the incident portion of the light beam 200 may overlap a hypothetical plane which is orthogonal to both of the two orthogonal mirrors.

Mirror arrangements comprising three orthogonal mirrors, corner cube prisms, Luneburg lenses or retroreflective films may be utilized almost independently of the orientation of the incident light beam 200.

In the optical system 100'-1 according to the first example embodiment of the first example aspect herein (or the described variant thereof), each of the reflectors 210 has a projected area (as shown at 290 in FIG. 4*c*, for example), which is defined as the two-dimensional projection of the respective reflector in the direction of the respective reflection center axis 250. The projected area 290 of each of the reflectors 210 partially overlaps with the projected area 290 of at least one other of the reflectors 210. The overlapping projected areas 290 allow the light beam 200 to pass each of the reflectors. The reflection centre axis 250 of at least one of the reflectors 210 may intersect the projected area 290 of at least one other of the reflectors 210, thereby allowing the light beam 200 to pass at least one of the reflectors 210 multiple times.

In an optical system 100'-1 according to a first example embodiment (or the variant thereof) described above, at least one of the reflectors 210 is configured so as to be movable in an adjustment direction 220. Preferably, the adjustment direction 220 is parallel to the reflection center axis (250 *a*, 250 *b*, 250 *c* and 250 *d*) of the at least one of the reflectors 210 *a*, 210 *b*, 210 *c* and 210 *d*. Alternatively, the adjustment direction 220 may be inclined (for example, orthogonal) with respect to the reflection center axis. Adjustment direction 225 is provided as such an example. If the adjustment direction 220 is chosen so as to be parallel to the reflection center axis 250, continuous adjustment of the length of the light beam 200 may be possible. If, however, the adjustment direction is chosen so as to be orthogonal to the reflection center axis 250 (e.g., as illustrated by adjustment direction 225), the length of the light beam 200 may be varied in discrete steps. That is, in the latter case, the number of passes of the light beam 200 associated with at least one particular reflector 210 may be varied.

In an optical system 100'-1 according to a first embodiment (or the variant thereof) described herein, the light source 20 may be configured to provide, as the light beam 200, a light beam having a coherence length and a wavelength that would render an OCT imaging apparatus comprising the optical system 100'-1 (or 100'-1*) suitable for acquiring OCT images of a retina of an eye of a subject. The light source 20 may, for example, be configured to provide a light beam 200 having a coherence length between 1 and 10 meters, for example, between 1 and 2 meters. The light source 20 may further be configured to provide a light beam 200 of the infrared spectrum, i.e. a light beam having wavelengths from 800 to 1400 nm.

The optical system 100'-1 (or 100'-1*) may preferably comprise two, but not more than two, reflectors 210.

In the optical system 100'-1 according to a first embodiment (or the variant thereof) described herein, the number of reflectors required to obtain a particular light-travelling distance may be reduced relative to conventional optical systems. At least one of the effects described hereinafter may be associated with an optical system 100'-1 (or 100'-1*). The optical system 100'-1 or 100'-1* may be lighter than a conventional optical system, making it easier to easier to transport. Additionally or alternatively, since fewer reflectors are required, a small installation space may be obtained relative to an installation space of a conventional optical system. The optical system 100'-1 (or 100'-1*) may be less susceptible to errors, as a better reflection alignment could be achieved, as compared to conventional optical systems.

Embodiment 2

An optical system 100'-2 according to a second embodiment of the first example aspect herein is illustrated in FIG. 3c. The second example embodiment corresponds to the first embodiment but differs in the way in which the reflected portion of a light beam 200 is guided from the last reflector 210b to the light output device 240. Alternatively or additionally, the second example embodiment may differ from the first embodiment in the way in which the portion of the light beam 200 incident on the first reflector 210a is guided from the light input device 230 to the first reflector 210a.

The optical system 100'-2 according to the second example embodiment is structurally similar to the optical system 100'-1 according to the first embodiment described above, but additionally comprises at least one specular element 270 (in other words, a reflective element such as a mirror). The at least one specular element 270 is configured to reflect the light beam 200 such that the portion of the light beam 200 reflected by the specular element 270 and/or the portion of the light beam 200 incident on the specular element 270 are not parallel to the portions of the light beam 200 incident on any one of the reflectors 210a and 210b.

In the optical system 100'-2, the light beam 200 may be reflected by a specular element 270 after being last reflected from the last reflector 210b (see FIG. 3c). The light beam 200 may thus be prevented from passing at least one of the reflectors 210a and 210b any more times. Instead, the light beam 200 may be diverted to outside of the optical system 100'-2. The specular element 270 may therefore act as an output element to extract the light beam 200 from the optical system 100'-2.

Likewise, the light beam 200 may first be incident on a particular portion of a first reflector 210a, on which the light beam 200 could hardly or not be incident in absence of the specular element 270. That is because, in some cases, another reflector may be in the way if a light beam 200 were to be directly aimed at such a particular portion. For example, the configuration of FIG. 3c could be operated in reverse, with specular element 270 acting as an input element to introduce the light beam 200 to the optical system 100'-2, rather than as an output element. It is noted that the latter case is not depicted in FIG. 3c, but nevertheless forms part of the present disclosure.

In the example embodiment depicted in FIG. 3c, the portion of the light beam 200 reflected by the specular element 270 is perpendicular to the portion of the light beam 200 first incident on the first reflector 210a. However, the portion of the light beam 200 reflected by the specular element 270 and the portion of the light beam 200 first incident on the first reflector 210a may alternatively form any angle between 0 and 90°, wherein 0° is excluded and 90° is included. Examples of such an angle may be, without limitation, 60° 45°, 30°, 20°, or 10°.

The specular element 270 may further be configured such that it at least partially reflects a light beam 200 incident on one side thereof, and at least partially allows transmission of a light beam 200 incident on another side thereof.

The specular element 270 may further be configured such that only a small portion thereof, e.g. a portion having an area of 1 mm$^2$, reflects an incident light beam 200, whereas the rest of the specular element 270 allows transmission of a light beam 200.

It is further noted that the definitions and variations described in the framework of the first example embodiment of the first example aspect herein may also be applied on the second example embodiment of the first example aspect herein as described above. Likewise, similar or equal technical effects may be obtained.

Embodiment 3

An optical system 100'-3 according to a third example embodiment of the first example aspect herein is illustrated in FIG. 3d. The third example embodiment corresponds to the first example embodiment of the first example aspect but differs in the way in which the portion of the light beam 200 last reflected from the last reflector is guided to the light output device 240. Alternatively or additionally, the third example embodiment may differ from the first embodiment in the way in which the light beam 200 is guided to the first reflector.

In the optical system 100'-3, at least one of the reflectors 210e and 210f is provided with at least one reflecting surface 280 and at least one light beam passage 260. The at least one light beam passage 260 is located on the at least one reflecting surface 280 of the at least one reflector. Further, the at least one light beam passage 260 is configured to allow transmission of the light beam 200 therethrough. As depicted in FIG. 3d, the light beam passage 260 may be formed by an opening extending through the respective reflecting surface 280 and through the entire reflector 210e. The light beam passage 260 may be aligned with, or may enclose, the reflection centre axis 250. However, alternatively or additionally, in the optical system 100'-3, the light beam passage 260 may be formed by locally altering a portion of the reflecting surface 280 such that the portion of the light beam 200 incident on the altered portion is transmitted through said portion.

In the embodiment depicted in FIG. 3d, the portion of the light beam 200 last reflected by the last reflector 210f is transmitted through the light beam passage 260, which is formed in the reflector 210e. The light beam 200 may thus be prevented from passing at least one of the reflectors 210e and 210f more times. The light beam passage 260 acts as an output element to extract the light beam 200 from the optical system 100'-3.

Likewise, in another example embodiment herein, the light beam 200 may first be incident on a reflector after having been transmitted through a light beam passage 260 formed in another reflector 210. In such an alternative embodiment, the light beam 200 may be incident on a portion of the first reflector 210, on which the light beam 200 could hardly be incident in absence of the light beam passage 260 (that may be because, in some example cases, another reflector may be in the way if the light beam 200 were to be directly aimed at such a particular portion). For example, the configuration of FIG. 3d could be operated in reverse, with beam passage 260 acting as an input element to introduce the light beam 200 to the optical system 100'-3, rather than an output element. It is noted that the latter case is not depicted in FIG. 3c, but nevertheless forms part of the present disclosure.

Examples of light beam passages 260 that may be utilized in an optical system 100'-3 according to the third embodiment of the first example aspect herein are depicted in FIGS. 5a, 5b, 5c and 5d. By way of example, FIGS. 5a and 5b depict reflectors in the form of corner cube prisms, 210-5 and 210-6, each having three reflective surfaces, 280a, 280b and 280c. Each of the reflective surfaces 280a, 280b and 280c is orthogonal to the other two reflective surfaces. In FIGS. 5a and 5b, the light beam 200 is incident on a first reflective surface 280a and reflected by the first reflective surface 280a such that it is incident on a second reflective surface 280b. Subsequently, the light beam 200 is reflected by the second reflective surface 280b such that it is incident on a third reflective surface 280c. The light beam 200 is then reflected by the third reflective surface 280c so that the portion of the light beam 200 finally reflected by the corner cube prism is parallel to the portion of the light beam 200 that is incident on the first reflective surface 280a. A second light beam, 200x, is also incident on the corner cube prism. However, in the example of FIG. 5a, the second light beam 200x is incident on a light beam passage 260 formed on the reflective surface 280c. Thus, the second light beam 200x is transmitted through the corner cube prism 210-5. In the example of FIG. 5a, the light beam passage 260 is an altered portion of the reflective surface 280c that allows transmission of the light beam 200x. The example of FIG. 5b corresponds to the example of FIG. 5a, although the light beam passage 260-6 in the corner cube prism 210-6 illustrated in FIG. 5b is a physical opening that extends through the corner cube prism 210-6, thereby also providing an opening on the reflective surface 280c.

The examples depicted in FIGS. 5c and 5d are similar to the examples depicted in FIGS. 5a and 5b, respectively. However, in the examples of FIGS. 5c and 5d, corner cubes 210-7 and 210-8 each comprising three orthogonal mirrors, 211a, 211b and 211c, are utilized instead of corner cube prisms. It is noted that the three orthogonal mirrors 211a, 211b and 211c of FIGS. 5c and 5d provide respective reflective surfaces.

In the examples of FIGS. 5a, 5b, 5c, and 5d, the second light beam 200x may be a reflection of the first light beam 200 re-entering the depicted corner cube prism (or, in the case of FIGS. 5c and 5d, corner cube) due to reflection by another reflector 210, such as a corner cube prism (not shown).

It is further noted that the definitions and variations described in the framework of the first embodiment of the first example aspect herein may also be applied on the third embodiment of the first example aspect herein as described above. Likewise, similar or equal technical effects may be obtained.

Further Embodiments

In the embodiments described above, substantially three ways are described of how a light beam 200 may be treated before it is first incident on a first reflector 210. Likewise, substantially three ways are described of how a light beam 200 may be treated after it is last reflected from a last reflector. However, it is noted that each combination of the ways may be regarded as another embodiment of the first example aspect herein.

Optionally, according to another embodiment of the first example aspect herein, multiple optical systems of the same or of different embodiments of the first example aspect herein as described above may be serially connected in order to further increase the travelling distance of the respective light beam 200.

An optical delay line for an optical coherence tomography apparatus according to an embodiment of the second example aspect herein may comprise an optical system according to any of the embodiments of the first example aspect described above.

An optical coherence tomography apparatus according to an embodiment of a third example aspect herein may comprise an optical system according to any of the embodiments of the first example aspect described above, or the optical delay line according to the embodiment of the second example aspect as described above.

An optical coherence tomography apparatus according to an embodiment of a third example aspect herein may comprise elements of exemplary OCT-apparatuses, for example, those described above and shown in FIG. 1 and FIGS. 2a to 2c of the present application.

Figure 6:
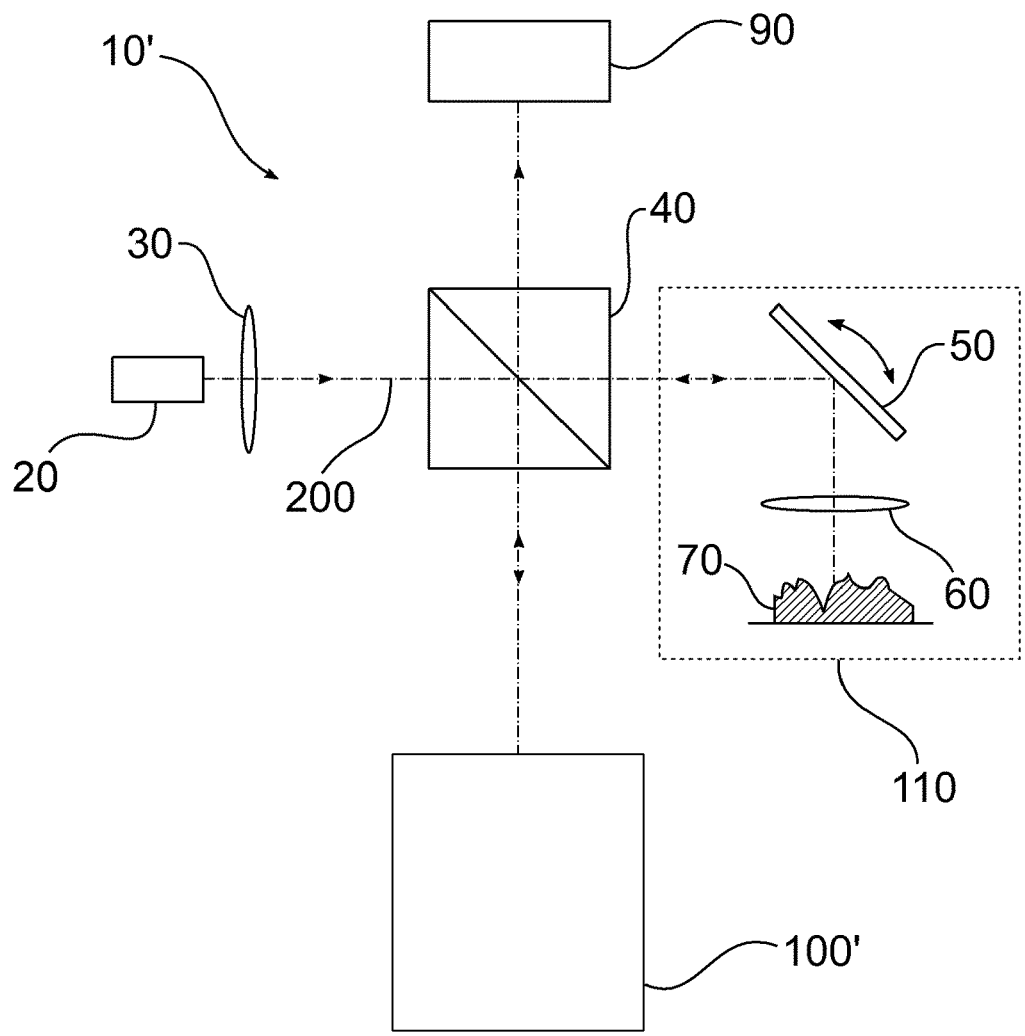
FIG. 6 schematically illustrates an optical coherence tomography apparatus according to an example embodiment of the third example aspect herein.

Reference is made to FIG. 6, depicting an OCT apparatus 10' according to an embodiment of the third example aspect herein. The OCT apparatus 10' may comprise a light source 20 configured to provide a light beam 200, a first collimator device 30 configured to collimate the light beam 200 provided by the light source 20 and at least one beam splitter 40 configured such that the light beam 200 incident on the beam splitter 40 is partially reflected by, and partially transmitted through the beam splitter 40. One of the reflected and transmitted light beams 200 may be incident on, and reflected by, a substrate 70. The other one of the reflected and the transmitted light beams 200 may be incident on an, or guided to, an optical system according to any embodiment of the first example aspect as described above (labelled 100' in FIG. 6), or the optical delay line according to the embodiment of the second example aspect of the present application as described above.

It is noted that the light source 20 of the OCT apparatus may be the light source 20 of the optical system 100' according to any embodiment of the first example aspect of the present application as described above, or the optical delay line according to the embodiment of the second example aspect of the present application as described above.

Before being incident on, and reflected by a substrate 70, the light beam 200 may be reflected by a scanning mirror 50 configured to be movable in one or more directions.

Also, a second collimator device 60 may be provided, the second collimator device 60 being configured to collimate the light beam 200 incident on, and reflected by the substrate 70.

The OCT apparatus 10' may further comprise a detector unit 90 configured to detect light of the light beam 200 reflected by substrate 70 and light of the light beam 200 provided by the optical system 100'. The detector unit 90 may be configured to detect an interference pattern between the light reflected by the substrate 70 and the light provided by the optical system 100'. The detector unit 90 may further be configured to obtain depth information of the substrate 70 based on the interference pattern.

An optical delay line according to an embodiment of the second example aspect of the present application and/or the optical coherence tomography apparatus according to the embodiment of the third example aspect of the present application may be associated with equivalent or similar effects as it has been described with respect to the optical system 100' according to the first example aspect of the present application.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Having now described some illustrative embodiments and embodiments, it is apparent that the foregoing is illustrative and not limiting, having been presented by way of example.

The devices and apparatus described herein may be embodied in other specific forms without departing from the characteristics thereof. The foregoing embodiments are illustrative rather than limiting of the described systems and methods. Scope of the optical systems and apparatuses described herein is thus indicated by the appended claims, rather than the foregoing description, and changes that come within the meaning and range of equivalence of the claims are embraced therein.

The invention claimed is:

1. An optical system, capable to admit a light beam, the optical system comprising:
a plurality of reflectors comprising a first reflector and a second reflector, the plurality of reflectors being configured to reflect the light beam wherein:
each of the reflectors is configured to reflect an incident light beam according to a number of passes, such that, for each pass of the number of passes, a path of the incident light beam and a path of the reflected light beam are parallel to each other;
each of the reflectors has a reflector center axis positioned centrally between the path of the incident light beam and the path of the reflected light beam; and
the first reflector and the second reflector are arranged relative to each other such that their respective reflector center axes do not overlap, thereby enabling the path of the light beam to pass at least one of the first reflector or the second reflector multiple times; and
in operation of the optical system:
the light beam reflected from the first reflector is incident on the second reflector and reflected by the second reflector back to the first reflector;
the light beam is incident on the first reflector first, before being incident on any other of the reflectors;
the light beam is last reflected by the first reflector such that, after the last reflection from the first reflector, the light beam is not incident on any other of the reflectors; and
at least one of the first reflector or the second reflector is movable in an adjustment direction that is orthogonal to its respective reflector center axis, thereby changing the number of passes in which incident light and reflected light are parallel, to permit a length of the light beam between the first reflector and the second reflector to be adjusted in discrete steps according to the changed number of passes.

2. The optical system of claim 1, further comprising a specular element configured to reflect the light beam such that at least one of a path of the light beam reflected by the specular element or a path of the light beam incident on the specular element is not parallel to a path of the light beam incident to any one of the reflectors.

3. The optical system of claim 1, wherein at least one of the path of the first light beam incident on the first reflector, or the path of the last light beam reflected by the first reflector, is not incident on the second reflector.

4. The optical system of claim 1, wherein each of the reflectors comprises a respective one of:
a mirror arrangement comprising two orthogonal mirrors;
a corner cube comprising three orthogonal mirrors;
a corner cube prism; or
a Luneburg lens.

5. The optical system of claim 1, wherein at least one of the reflectors is configured so as to be movable in an adjustment direction, the adjustment direction being parallel to the reflector center axis of the at least one reflector.

6. The optical system of claim 1, further comprising a light source configured to provide the light beam.

7. The optical system of claim 1, wherein the optical system further comprises at least one of a light input device or a light output device, and wherein, in operation of the optical system, at least one of:
the path of the light beam first incident on the first reflector emerges from the light input device; or
the path of the light beam last reflected by the first reflector is incident on the light output device.

8. The optical system of claim 7, wherein the light input device comprises an input fibre collimator.

9. The optical system of claim 7, wherein the light output device comprises an output fibre collimator.

10. The optical system of claim 1, wherein at least one of the reflectors is provided with at least one reflecting surface and at least one light beam passage said light beam passage being located on the at least one reflecting surface and being configured to allow transmission of the light beam therethrough.

11. The optical system of claim 10, wherein, in operation of the optical system, at least one of the path of the light beam first incident on the first reflector or the path of the light beam last reflected by the first reflector, passes through the at least one light beam passage.

12. The optical system of claim 1, wherein:
   each of the reflectors has a projected area, said projected area being defined as a two-dimensional projection of the respective reflector in a direction of a respective reflector center axis, and
   the projected area of each of the reflectors at least partially overlaps with the projected area of at least one other of the reflectors.

13. The optical system of claim 12, wherein the reflector center axis of at least one of the reflectors intersects the projected area of at least one other of the reflectors.

14. An optical delay line for an optical coherence tomography apparatus, the optical delay line comprising an optical system capable to admit a light beam, the optical system comprising:
   a plurality of reflectors comprising a first reflector and a second reflector, the plurality of reflectors being configured to reflect the light beam, wherein:
      each of the reflectors is configured to reflect an incident light beam according to a number of passes, such that, for each pass of the number of passes, a path of the incident light beam and a path of the reflected light beam are parallel to each other;
      each of the reflectors has a reflector center axis positioned centrally between the path of the incident light beam and the path of the reflected light beam; and
      the first reflector and the second reflector are arranged relative to each other such that their respective reflector center axes do not overlap, thereby enabling the path of the light beam to pass at least one of the first reflector or the second reflector multiple times; and
   in operation of the optical system:
      the light beam reflected from the first reflector is incident on the second reflector and reflected by the second reflector back to the first reflector;
      the light beam is incident on the first reflector first, before being incident on any other of the reflectors;
      the light beam is last reflected by the first reflector such that, after the last reflection from the first reflector, the light beam is not incident on any other of the reflectors; and
      at least one of the first reflector or the second reflector is movable in an adjustment direction that is orthogonal to its respective incident and reflected light beam paths, thereby changing the number of passes for the reflector, to permit a length of the light beam between the first reflector and the second reflector to be adjusted in discrete steps.

15. The optical delay line of claim 14, wherein at least one of the reflectors is provided with at least one reflecting surface and at least one light beam passage said light beam passage being located on the at least one reflecting surface and being configured to allow transmission of the light beam therethrough.

16. The optical delay line of claim 14, wherein at least one of the reflectors is configured so as to be movable in a second adjustment direction, the parallel to its respective incident and reflected light beam paths.

17. An optical coherence tomography apparatus comprising an optical system capable to admit a light beam, the optical system comprising:
   a plurality of reflectors comprising a first reflector and a second reflector, the plurality of reflectors being configured to reflect the light beam, wherein:
      each of the reflectors is configured to reflect an incident light beam according to a number of passes, such that, for each pass of the number of passes, a path of the incident light beam and a path of the reflected light beam are parallel to each other;
      each of the reflectors has a reflector center axis positioned centrally between the path of the incident light beam and the path of the reflected light beam; and
      the first reflector and the second reflector are arranged relative to each other such that their respective reflector center axes do not overlap, thereby enabling the path of the light beam to pass at least one of the first reflector or the second reflector multiple times; and
   in operation of the optical system:
      the light beam reflected from the first reflector is incident on the second reflector and reflected by the second reflector back to the first reflector;
      the light beam is incident on the first reflector first, before being incident on any other of the reflectors;
      the light beam is last reflected by the first reflector such that, after the last reflection from the first reflector, the light beam is not incident on any other of the reflectors; and
      at least one of the first reflector or the second reflector is movable in an adjustment direction that is orthogonal to its respective reflector center axis, thereby changing the number of passes in which incident light and reflected light are parallel, to permit a length of the light beam between the first reflector and the second reflector to be adjusted in discrete steps according to the changed number of passes.

18. The optical coherence tomography apparatus of claim 17, wherein at least one of the reflectors is configured so as to be movable in a second adjustment direction parallel to the reflector center axis of the at least one reflector.

19. An optical coherence tomography apparatus comprising an optical delay line, the optical delay line comprising an optical system capable to admit a light beam, the optical system comprising:
   a plurality of reflectors comprising a first reflector and a second reflector, the plurality of reflectors being configured to reflect the light beam, wherein:
      each of the reflectors is configured to reflect an incident light beam according to a number of passes, such that, for each pass of the number of passes, a path of the incident light beam and a path of the reflected light beam are parallel to each other;
      each of the reflectors has a reflector center axis positioned centrally between the path of the incident light beam and the path of the reflected light beam; and
      the first reflector and the second reflector are arranged relative to each other such that their respective reflector center axes do not overlap, thereby enabling the path of the light beam to pass at least one of the first reflector or the second reflector multiple times; and
   in operation of the optical system:
      the light beam reflected from the first reflector is incident on the second reflector and reflected by the second reflector back to the first reflector;
      the light beam is incident on the first reflector first, before being incident on any other of the reflectors;
      the light beam is last reflected by the first reflector such that, after the last reflection from the first reflector, the light beam is not incident on any other of the reflectors; and
      at least one of the first reflector or the second reflector is movable in an adjustment direction that is orthogonal to its respective reflector center axis, thereby changing the number of passes in which incident light and reflected light are parallel, to permit a length of the light beam between the first reflector and the second reflector to be adjusted in discrete steps.

20. The optical coherence tomography apparatus of claim 19, wherein at least one of the reflectors is configured so as to be movable in a second adjustment direction parallel to the reflector center axis of the at least one reflector.

* * * * *